United States Patent
Cleuziat et al.

(10) Patent No.: US 7,723,095 B2
(45) Date of Patent: May 25, 2010

(54) METHOD FOR CELLULAR LYSIS OF PROKARYOTES OR EUKARYOTES OR SIMULTANEOUS CELLULAR LYSIS OF PROKARYOTES AND EUKARYOTES

(75) Inventors: Philippe Cleuziat, Lyons (FR); Sandra Incardona, Lyons (FR); Corinne Jay, Villeurbanne (FR)

(73) Assignee: Biomerieux S.A., Mary l'Etoile (FR)

( * ) Notice: Subject to any disclaimer, the term of this patent is extended or adjusted under 35 U.S.C. 154(b) by 974 days.

(21) Appl. No.: 10/343,109

(22) PCT Filed: Jul. 26, 2001

(86) PCT No.: PCT/FR01/02442

§ 371 (c)(1), (2), (4) Date: Apr. 18, 2003

(87) PCT Pub. No.: WO02/10333

PCT Pub. Date: Feb. 7, 2002

(65) Prior Publication Data

US 2003/0180938 A1   Sep. 25, 2003

(51) Int. Cl.
*C12N 1/00* (2006.01)
(52) U.S. Cl. .................. 435/243; 435/173.7; 435/306.1
(58) Field of Classification Search .................. 435/325, 435/259, 29

See application file for complete search history.

(56) References Cited

U.S. PATENT DOCUMENTS

| 5,643,767 | A  | * | 7/1997  | Fischetti et al. | ............ 435/91.3 |
| 6,391,541 | B1 | * | 5/2002  | Petersen et al.  | ................ 435/5 |
| 6,632,662 | B1 | * | 10/2003 | Broyer et al.    | ............ 435/306.1 |

FOREIGN PATENT DOCUMENTS

| WO | WO 99/15621 | 4/1999 |
| WO | WO 00/05338 | 2/2000 |

OTHER PUBLICATIONS

Hirose et al., Biotechnology Techniques, 1999, vol. 13, p. 571-575.*
Chisti & Moo-Young, Biotechnology: The Science & The Business, 2nd edition, 1999, Chapter 13, p. 177-222.*

* cited by examiner

*Primary Examiner*—L Blaine Lankford
*Assistant Examiner*—Kade Ariani
(74) *Attorney, Agent, or Firm*—Daniel A. Monaco; Drinker Biddle & Reath LLP (57) ABSTRACT

A method for lysing prokaryotic or eukaryotic cells, or for simultaneous lysis of both, which includes at least three of the following: a mass of active, small-diameter beads corresponding to 50% or less than a mass of active, larger-diameter beads, and/or a total mass of lysing beads (consisting of a single type of bead or a mixture of smaller and larger beads) corresponding to between 50 and 100% of the total mass of the processed biological sample, and/or a lysis time of from 10 to 20 minutes, and/or seven or less non-lysing glass beads to drive the movement of the lysing beads, and/or from five to fifteen non-lysing iron beads to drive the movement of the lysing beads, depending on whether sonication, mechanical vortex centrifugation or magnetic vortex centrifugation is used.

9 Claims, 2 Drawing Sheets

METHOD FOR CELLULAR LYSIS OF PROKARYOTES OR EUKARYOTES OR SIMULTANEOUS CELLULAR LYSIS OF PROKARYOTES AND EUKARYOTES

This application is a U.S. National Stage of International application PCT/FR01/02442, filed Jul. 26, 2001.

This invention concerns methods for universal lysis suitable for the simultaneous lysis of both prokaryotic and eukaryotic cells, for three different techniques, namely sonication, mechanical vortex centrifugation, and magnetic vortex centrifugation.

The background art consists of documents which deal with each of the three above-mentioned techniques separately.

As far as sonication is concerned, the applicant submitted Patent Application FR99/04289 which describes a method in which the sonotrode is activated with the following characteristics:
- a sonication time of 10 to 15 minutes,
- a cycling ratio of between 40 and 60% (preferably 50%), and
- an output power of 10 to 30 W.

Such sonication is effective for lysing microorganisms such as bacteria and yeast cells. Nevertheless, results can be improved, as shown by this invention. The same is true for other background art documents such as EP-A-0.337.690 which mentions only one bacterium, namely *Listeria innocua*.

Mechanical vortex centrifugation has already been described in one of the applicant's previous patent applications. Application WO-A-99/15621 deals with a method for lysing a biological sample containing at least one microorganism, either a bacterium or a yeast. Lysis methods differ in terms of the diameter of the beads used which, for bacteria is of between 90 and 150 µm, preferably 100 µM, and for yeast cells, 500 µm. It should be noted that in this patent application, a mixture of different-sized zirconium beads was used, 50% with a diameter of 100 µm and the other 50% with a diameter of 500 µm (see FIGS. 1 and 2 protocol G) to lyse bacteria of the species *Staphylococcus epidermidis*.

Although the results obtained with this ratio of different-sized beads were satisfactory, they were not as good as those obtained with:
- glass beads of between 90 and 150 µm in diameter (Protocol C),
- glass beads with a diameter of 100 µm (Protocol D), or
- zirconium beads with a diameter of 100 µm (Protocol E).

The applicant has already described and claimed a device and a method for the lysis of microorganisms based on magnetic vortex centrifugation. Thus, in patent application WO-A-00/05338, the lysis device includes at least two different types of means of crushing with different dimensions:
- at least one larger, magnetized means, the movement of which is actuated in a magnetic field, and
- at least one smaller means, the movement of which is driven by the larger means of crushing.

The larger means of crushing is constituted by at least one bead with a large diameter, and the smaller means of crushing is constituted by at least one bead with a small diameter. The ratio between the size of the smaller means of crushing and the size of the larger means of crushing is between 1/10 and 1/100, preferably between 1/30 and 1/60 and, more exactly, this ratio is 1/40.

However, the applicant continued work on this technical problem and developed protocols for lysing all types of microorganism, be they prokaryotic (bacteria), eukaryotic (yeasts), or a mixture of prokaryotes and eukaryotes. These protocols—said to be universal—are as effective as lysis methods specifically designed for bacteria or yeasts such as those described in the above-mentioned background art. Surprisingly, in certain cases, these universal protocols often proved more effective than the lysis methods in the background art.

To this effect, this invention concerns a method for lysing prokaryotic or eukaryotic cells, or for the simultaneous lysis of both prokaryotic and eukaryotic cells, which consists in adapting at least three of the following parameters:
- a mass of active, small-diameter beads, corresponding to 50% or less than the mass of active, large-diameter beads, and/or
- a total mass of lysing beads (consisting of a single type of bead or a mixture of smaller and larger beads) corresponding to between 50 and 100% of the total mass of the processed biological sample, and/or
- a lysis time of between 10 and 20 minutes, and/or
- seven (7) or fewer non-lysing glass beads to drive the movement of the lysing beads, and/or
- between five (5) and fifteen (15) non-lysing iron beads to drive the movement of the lysing beads, depending on the technique being used:
- sonication,
- mechanical vortex centrifugation, or
- magnetic vortex centrifugation.

According to a preferred embodiment, the lysing beads are made of glass.

According to another preferred embodiment, the diameter of the smaller lysing beads is between 90 and 150 µm and preferably of about 100 µm, and the diameter of the larger lysing beads is between 400 and 600 µm and preferably of about 500 µm.

If the sonication technique is used, the method consists in achieving lysis with the following parameters:
- a lysis time of between 9 and 20 minutes, preferably between 12 and 18 minutes, and more preferably still of 15 minutes,
- a percentage of beads with a diameter of 100 µm of between 10 and 50%, preferably between 20 and 30%, and more preferably still of 20%, and
- a total mass of lysing beads corresponding to between 50 and 100% of the total mass of the processed biological sample, preferably between 75 and 90%, and more preferably still between 80 and 85%.

If the mechanical vortex centrifugation technique is used, the method consists in achieving lysis with the following parameters:
- a lysis time of between 11 and 20 minutes, preferably between 15 and 20 minutes, and more preferably still of 20 minutes,
- a percentage of beads with a diameter of 100 µm of under 50%, preferably under 30%, and more preferably still of 20%, and
- a total mass of lysing beads of over 60%, preferably over 80%, and more preferably still of 100% of the total mass of the processed biological sample, and
- less than seven (7) glass beads, preferably just one (1).

If the magnetic vortex centrifugation technique is used, the method consists in achieving lysis with the following parameters:
- a lysis time of between 12 and 20 minutes, preferably between 15 and 20 minutes, and more preferably still of 20 minutes, a total mass of lysing beads with a diameter of 100 μm of over 80% and preferably of 100% of the total mass of the processed biological sample, and between five (5) and fifteen (15) iron beads, preferably ten (10) iron beads.

The accompanying drawings are given by way of example and are not to be taken as limiting in any way. They are designed to make the invention easier to understand.

Finally.

I. MATERIALS AND METHODS

As mentioned in the background art, three techniques are known, namely sonication, mechanical vortex centrifugation, and magnetic vortex centrifugation. Each has been independently defined for the lysis of either bacterial cells or yeast cells. The parameters defined here for each shown in Table 1 are in keeping with the parameters deemed correct in the background art. It should be noted that the volume of all the biological samples treated—be it using the reference protocols or the protocols according to this invention—is 600 μl.

TABLE 1

Lysis protocols according to the background art, referred to as reference protocols

| Factor | Protocol | | | | | |
|---|---|---|---|---|---|---|
| | Sonication | | Mechanical vortex centrifugation | | Magnetic vortex centrifugation | |
| | bacterial cells | yeast cells | bacterial cells | yeast cells | bacterial cells | yeast cells |
| Diameter (μm) and quantity of active beads | 100 and 0.4 | 500 and 0.3 | 100 and 0.6 | 500 and 0.5 | 100 and 0.6 | 500 and 0.5 |
| Number of glass beads (diameter = 3 mm) | / | / | 6 | | / | / |
| Number of iron beads (diameter = 2 mm) | / | / | 10 | | 10 | |
| Lysis time | 15 min. | | 2 min. | 12 min. | 10 min. | 12 min. |

The active beads described as "lysing" beads correspond to beads which mediate lysis of the microorganisms. These beads have a relatively small diameter (100 or 500 μm). It should be noted that the glass beads with a diameter of 100 μm are obtained from Masteau & Lamarie, Paris, France (reference: Via 1), and that the glass beads with a diameter of 500 μm are supplied by Sigma, St. Louis, Mo., USA (reference: 8772).

In contrast, the purpose of the other glass beads (with a diameter of 3 mm) or the iron beads (with a diameter of 2 mm) used in mechanical and magnetic vortex centrifugation is to drive the movement of the active beads during lysis. These are referred to as the passive beads, since they are only indirectly active via the above-defined active beads. The glass beads with a diameter of 3 mm are bought from Prolabo, Fontenay-sous-Bois, France, (reference: 00680032), and the iron beads with a diameter of 2 mm are obtained from Bennk Elektronic, Norderstadt, Germany (reference: 050-330).

It should be noted that the iron beads can be coated with a biologically inert material such as plastic or glass in order to isolate the metal and prevent any leaching which can compromise subsequent operations in which the nucleic acids released during lysis are amplified.

In the following, the results obtained using the methods according to the invention will be compared with those obtained using the above-described reference methods.

The value of a universal lysis protocol is to make possible the detection of microorganisms in normally sterile biological fluids (e.g. cerebrospinal fluid, urine or blood), without prior knowledge of whether the microorganism concerned is prokaryotic (a bacterium) or eukaryotic (a yeast).

A) Experimental Research Methodology

An Experimental Research Methodology (ERM) approach was adopted for sonication and mechanical vortex centrifugation. An experimental approach was adopted for magnetic vortex centrifugation.

The ERM study includes two steps. Firstly, for various factors, an optimum range is defined for yeast and another optimum range is defined for bacteria. This optimum range is defined as that in which lytic efficacy is equivalent or superior to that observed with the reference protocol.

Secondly, a so-called overlap range, corresponding to the range in which the optimum range for bacteria coincides with the optimum range for yeast, is defined (if such an overlap exists).

ERM is a mathematical approach which involves modeling a biological phenomenon—lysis, in this case—in the form of a mathematical equation (often a second degree polynomial equation) of the following type:

$R = aX + bY + cX^2 + dY^2 + eXY + f$, in which

R is the experimental response corresponding to the efficacy of lysis,

X and Y are factors which affect lysis such as lysis time and bead size, and a, b, c, d, e and f are coefficients.

Figures 1, 2, 3:
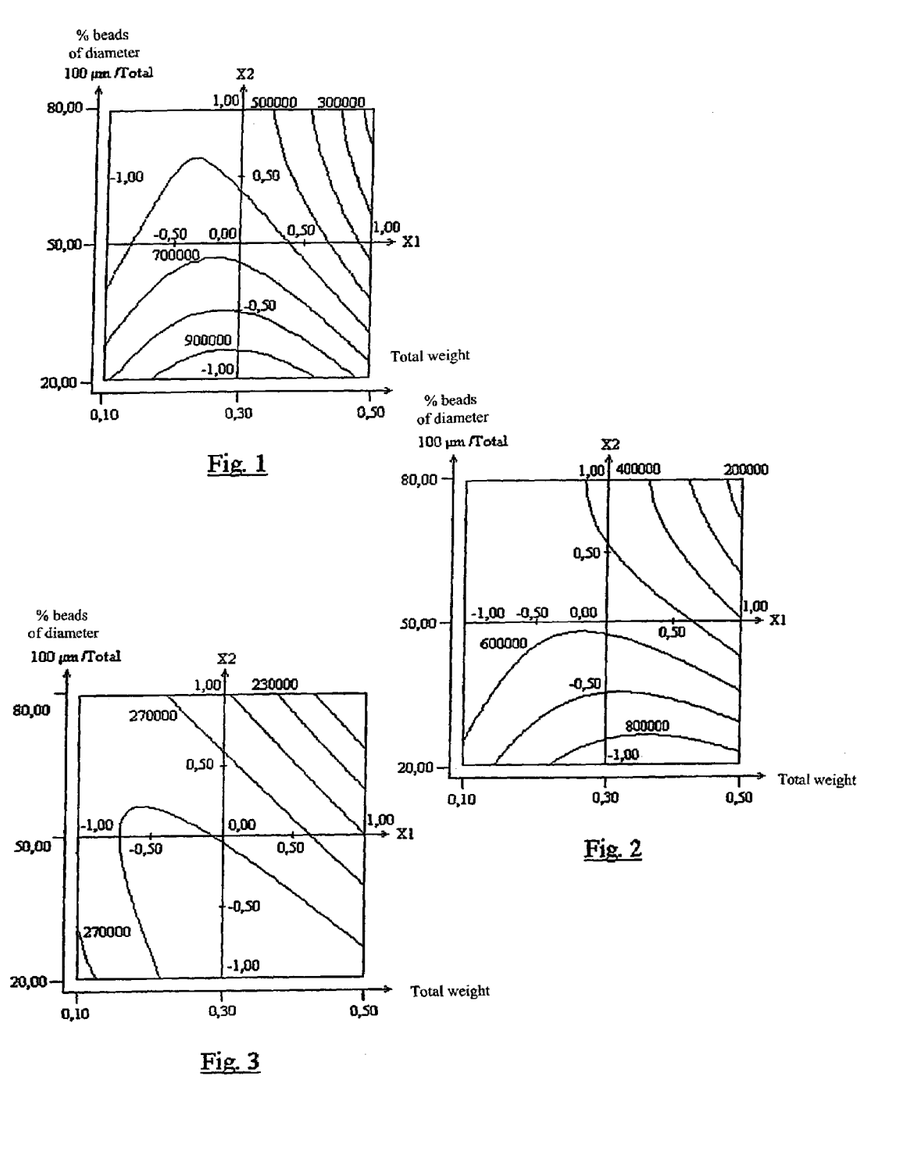
FIG. 1 shows an example of isoresponse curves for an ERM approach.
FIG. 2 shows isoresponse curves for the lysis of yeast cells by sonication.
FIG. 3 shows isoresponse curves for the lysis of bacterial cells by sonication.

This equation can be represented in the form of graphs referred to as isoresponse curves, which show how responses vary as a function of different values for the various factors. FIG. 1 gives an example of some isoresponse curves.

In FIG. 1, two factors are being studied. These factors are the overall weight (X1) of all the lysing beads (i.e. the beads with diameters of both 100 μm and 500 μm), and the percentage of this overall weight represented by only the beads with a diameter of 100 μm (X2); the response is expressed in fluorescence units, i.e. Relative Light Units (RLU). The curves plotted join all points in the experimental range which correspond to the same response. This graph shows that the maximum response obtained in the experimental range is one of 900,000 fluorescence units, and that in order to obtain this response, the value of X1 must be between 0.2 and 0.4, and that of X2 close to 20.

Generating the mathematical model necessitates conducting a number of preliminary experiments defined by matrices referred to as "composite matrices" which are thoroughly described in the following documents:

Box and Wilson (1951) "On the experimental attainment of optimal conditions" Journal of the Royal Statistical Society, B, 13, p. 1-45.

Feneuille, Mathieu, Phan-Tan-Lun (1978) <<Méthodologie de la Recherche Expérimentale. Introduction, outils mathématiques, études des surfaces de réponse, matrices de mélanges; méthodes du simplex; "*Experimental Research Methodology. Introduction, mathematical instruments, the study of response surfaces, mixed matrices; simplex methods*; Université d'Aix-Marseille 3—Publication of the LMRE.

B) Response Studied

Lytic efficacy is assayed by measuring the amount of released 16S and 23S RNA (for bacteria), or ribosomal RNA (for yeast) by hybridization with a chemiluminescent probe. The actual measurement is based on a hybridization protection assay (HPA). The method was developed by GenProbe and is comprehensively described in the article by Norman C. Nelson, Mark A. Reynolds et Lyle J. Arnold Jr: <<(Detection of Acridinium Esters by Chemiluminescence>> *Nonisotropic probing, Blotting and Sequencing* (1995) 391-428. Further information on this method can be found in U.S. Pat. No. 6,004,745.

Two probes are used, one of which was developed by GenProbe and is sold under the name Mycoplasma Tissue Culture NI (MTC-NI), see their catalogue: 104574 Claim. A. As stated on page 3 in the Chapter on "Performance Characteristics", this probe can be used to detect a wide variety of different Gram-positive and Gram-negative bacteria without any cross-reactivity with eukaryotic targets.

A second probe was used for yeasts. It is possible to use a probe such as those described by:

J. F. Hindler, S. Kozen, D. A. Bruckner in the article: <<Application of an rRNA Probe Matrix for Rapid Identification of Bacteria and Fungi in Routine Blood Cultures>> N° 1557, et D. D. Fuller, T. E. Davis in the article: <<(Comparison of rRNA Probe Matrix to Conventional Methods for Rapid Identification of Clinically Significant Bacteria and Fungi Recovered from Blood Cultures Specimens>> N°1558, in session 154.D, page 221, Laboratory Tests for Diagnosing Infections; Methods for susceptibility testing.

Abstracts book, ICAAC—Sept. 26-29, 1999—San Francisco—USA—Two posters presenting the use of a universal probe able to detect all fungal species (both molds and yeasts).

C) Factors Studied

The factors that can be investigated are:

the total weight of active beads (in grams), the percentage of the overall bead weight accounted for by lysing beads with a diameter of 100 μm, lysis time (in minutes), the number of added glass beads with a diameter of 3 mm, and the number of added iron beads with a diameter of 2 mm.

D) Strains of Yeast and Bacteria Used

The yeast strain chosen for the experiments was *Candida krusei*, the bioMérieux Collection number of which is: API n° 9604191. The bacterial strain was *Mycobacterium fortuitum*, the ATCC registration number of which is: 49403.

Lysis was carried out on 600 μl aliquots of a suspension at a density of 0.5 MacFarland (bioMérieux densitometer).

II. PRELIMINARY RESULTS USING THE REFERENCE METHODS

A) Results Showing the 100 μm Beads to be More Effective Than the 500 μm Beads for Bacterial Lysis The results are shown in Table 2 below; all units are expressed in terms of HPA, as in the following Tables (3 through 10).

TABLE 2

Comparison of the 100 μm beads and the 500 μm beads using the three techniques for bacterial lysis

|  | Active beads with a diameter of 100 μm | | Active beads with a diameter of 500 μm | |
| --- | --- | --- | --- | --- |
|  | Readings | Mean | Readings | Mean |
| Sonication | 125,382 | 125,180 | 75,607 | 84,428 |
|  | 105,474 |  | 95,799 |  |
|  | 120,807 |  | 93,081 |  |
|  | 149,057 |  | 73,225 |  |
| Mechanical vortex centrifugation | 105,263 | 100,513 | 39,624 | 43,946 |
|  | 96,142 |  | 41,879 |  |
|  | 97,875 |  | 50,584 |  |
|  | 102,771 |  | 43,697 |  |
| Magnetic vortex centrifugation | 83,400 | 78,213 | 27,744 | 28,012 |
|  | 83,798 |  | 28,285 |  |
|  | 69,290 |  | 28,475 |  |
|  | 76,362 |  | 27,542 |  |

It is evident that, for all three techniques, the 100 μm beads are more effective than the 500 μm beads.

B) Results Comparing the Performance of 500 μm Beads and 100 μm Beads for the Lysis of Yeast Cells Some representative results are presented in Table 3 below.

TABLE 3

Comparison of the 100 μm beads and the 500 μm beads using the three techniques for the lysis of yeast cells

|  | Active beads with a diameter of 100 μm | | Active beads with a diameter of 500 μm | |
| --- | --- | --- | --- | --- |
|  | Readings | Mean | Readings | Mean |
| Sonication | 614,668 | 452,564 | 1,487,786 | 1,366,451 |
|  | 391,942 |  | 1,448,239 |  |
|  | 567,756 |  | 1,281,148 |  |
|  | 258,648 |  | 1,294,420 |  |
|  | 429,805 |  | 1,320,663 |  |
| Mechanical vortex centrifugation | 1,392,101 | 1,317,454 | 2,464,220 | 2,565,353 |
|  | 1,511,603 |  | 2,598,929 |  |
|  | 1,493,588 |  | 2,234,830 |  |
|  | 1,128,468 |  | 2,695,394 |  |
|  | 1,061,514 |  | 2,833,394 |  |

TABLE 3-continued

Comparison of the 100 μm beads and the 500 μm beads using the three techniques for the lysis of yeast cells

|  | Active beads with a diameter of 100 μm | | Active beads with a diameter of 500 μm | |
| --- | --- | --- | --- | --- |
|  | Readings | Mean | Readings | Mean |
| Magnetic vortex centrifugation | 1,688,929 | 1,543,208 | 1,026,887 | 1,131,101 |
|  | 1,853,702 |  | 1,192,650 |  |
|  | 1,361,236 |  | 970,409 |  |
|  | 1,362,156 |  | 1,097,997 |  |
|  | 1,450,016 |  | 1,367,563 |  |

For sonication and mechanical vortex centrifugation, the 500 μm beads are more effective for the lysis of yeast cells. But for magnetic vortex centrifugation, the 100 μm beads are more effective.

For sonication and mechanical vortex centrifugation, a universal protocol necessarily requires a mixture of beads with diameters of both 100 μm and 500 μm. In contrast, for magnetic vortex centrifugation, the two sizes do not need to be mixed together since 100 μm beads are the more effective for both bacterial and yeast cells.

III. RESULTS FOR LYSIS BY SONICATION ACCORDING TO THE INVENTION

Two factors are used, namely the total mass of lysing beads and the percentage of the total mass represented by beads with a diameter of 100 μm.

A) Sonication and Yeast Cells

In three experiments, the reference protocol (with the total mass of lysing beads=0.3 grams (g) and the percentage of the total mass represented by beads with a diameter of 100 μm=0%) gave the following results: 2 264 515, 1 821 135 and 1 505 887, i.e. a mean result of 1 863 846

The results are presented in Table 4 below.

TABLE 4

Comparison of the reference method and methods which could meet the criteria of this invention for the sonication of yeast cells

| Masse | Percentage of 100 μm beads | | | | | |
| --- | --- | --- | --- | --- | --- | --- |
| Total mass of lysing | 20% | | 50% | | 80% | |
| beads | Readings | Mean | Readings | Mean | Readings | Mean |
| 0.1 | 1,292,794 | 1,322,991 | 1,220,036 | 1,182,919 | 595,207 | 955,668 |
|  | 1,161,495 |  | 1,362,230 |  | 1,054,355 |  |
|  | 1,476,144 |  | 1,054,256 |  | 1,233,330 |  |
|  | 1,205,671 |  | 809,459 |  | 1,019,397 |  |
|  | 1,478,850 |  | 1,468,613 |  | 876,052 |  |
| 0.3 | 1,454,421 | 1,407,117 | 1,289,100 | 1,331,139 | 912,332 | 912,904 |
|  | 1,104,398 |  | 1,266,980 |  | 692,731 |  |
|  | 1,208,753 |  | 1,316,456 |  | 745,533 |  |
|  | 1,399,980 |  | 1,452,021 |  | 1,301,020 |  |
|  | 1,868,031 |  |  |  |  |  |
| 0.5 | 1,704,912 | 1,650,238 | 852,939 | 1,252,013 | 213,745 | 415,853 |
|  | 1,656,852 |  | 1,267,203 |  | 604,487 |  |
|  | 1,266,184 |  | 1,155,399 |  | 429,326 |  |
|  | 1,861,236 |  | 1,732,513 |  |  |  |
|  | 1,762,006 |  |  |  |  |  |

The maximum response is obtained with a percentage of 100 μm beads of 20%, and a total mass of lysing beads of 0.5 gram.

FIG. 2 shows the isoresponse curves. These isoresponse curves show that, to obtain a high response (800 000 fluorescence units), the total mass of lysing beads must be between 0.3 and 0.5 grams, and the percentage of 100 μm beads must be close to 20%.

B) Sonication and Bacteria

The reference protocol uses a total mass of lysing beads of 0.4 g and a percentage of 100 μm beads of 100%. This protocol gives the following readings: 264 915, 305 907 and 195 160, i.e. a mean reading of 255 327.

Table 5 shows all of the results obtained.

TABLE 5

Comparison of the reference method and methods which could meet the criteria of this invention for the sonication of bacteria

| Total mass of lysing beads | Percentage of 100 μm beads | | | | | |
|---|---|---|---|---|---|---|
| | 20% | | 50% | | 80% | |
| | Readings | Mean | Readings | Mean | Readings | Mean |
| 0.1 | 293,068 | 255,085 | 229,455 | 288,104 | 324,640 | 285,390 |
| | 199,178 | | 235,334 | | 323,472 | |
| | 213,691 | | 348,094 | | 254,815 | |
| | 248,425 | | 307,997 | | 220,425 | |
| | 321,064 | | 319,640 | | 303,600 | |
| 0.3 | 316,672 | 306,462 | 312,002 | 298,236 | 256,234 | 228,692 |
| | 322,443 | | 279,713 | | 126,639 | |
| | 325,418 | | 284,487 | | 303,203 | |
| | 313,086 | | 311,784 | | | |
| | 252,692 | | 303,192 | | | |
| 0.5 | 272,371 | 299,829 | 268,035 | 237,229 | 183,800 | 197,722 |
| | 294,345 | | 162,858 | | 138,313 | |
| | 350,986 | | 272,402 | | 271,054 | |
| | 261,954 | | 192,428 | | | |
| | 319,487 | | 290,421 | | | |

The maximum response is obtained with a percentage of 100 μm beads of 20%, and a total mass of lysing beads of between 0.3 and 0.5 g.

FIG. 3 shows the isoresponse curves. These curves show that, to obtain a high response, the total mass of lysing beads must be greater than 0.2 g, and the percentage of 100 μm beads must be between 20 and 50%.

C) Selecting a Universal Protocol for Lysis by Sonication

The universal protocol is therefore defined by the following parameters:
  percentage of beads with a diameter of 100% m=20%, and total mass of lysing beads=0.5 g.

In these conditions, the mean response obtained for bacteria is 299 829 which is greater than the mean of 255 327 obtained with the bacterium-specific reference protocol based on using only beads with a diameter of 100 μm. This is surprising, all the more so since the mean reading observed for yeast cells is 1 650 238, i.e. not much lower than the mean reading (1 863 846) obtained using the yeast-specific reference protocol based on using only 500 μm beads.

The method associated with this protocol consists therefore in performing sonication with the following parameters:
  a percentage of beads with a diameter of 100 μm of between 10 and 50%, preferably between 20 and 30%, and more preferably still of 20%, and
  a total mass of lysing beads corresponding to between 50 and 100% of the total mass of the processed biological sample, preferably between 75 and 90%, and more preferably still between 80 and 85%.

The percentage of the total mass of lysing beads with respect to the total mass of the processed biological sample is calculated in this section—as in the others—on the basis of 0.5 g of lysing beads for a 600 μl sample, i.e. substantially 0.6 g. The percentage is therefore: (0.5:0.6)×100=83.33%.

IV. RESULTS FOR LYSIS BY MECHANICAL VORTEX CENTRIFUGATION ACCORDING TO THE INVENTION

Four parameters are used: the percentage of beads with a diameter of 100 μm; the total mass of lysing beads of both 100 μm and 500 μm in diameter; the number of glass beads with a diameter of 3 mm; and lysis time (in minutes).

A) Mechanical Vortex Centrifugation and Yeast Cells

The reference protocol is based on a total mass of lysing beads of 0.3 g, a percentage of 100 μm beads of 0%, 6 glass beads, 10 iron beads, and a lysis time of 12 minutes. The HPA readings are 1 944 115, 2 213 485 and 2 158 958, i.e. a mean of 2 105 519.

The results are shown in Table 6.

TABLE 6

Comparison between the reference method and methods which could meet the criteria for this invention for the lysis of yeast cells

| Mass of lysing beads | Number of glass beads | Lysis time | Percentage of 100 μm beads | | | | | |
|---|---|---|---|---|---|---|---|---|
| | | | 20% | | 50% | | 80% | |
| | | | Readings | Mean | Readings | Mean | Readings | Mean |
| 0.1 g | 1 | 2 min. | 173,382 | 187,805 | NT = not tested | | 53,771 | 53,609 |
| | | | 198,469 | | | | 55,591 | |
| | | | 191,565 | | | | 51,464 | |
| | 13 | 2 min. | 383,782 | 635,628 | NT | | 566,150 | 559,011 |
| | | | 875,488 | | | | 631,271 | |
| | | | 647,615 | | | | 479,612 | |
| | 1 | 20 min. | 1,499,619 | 819,615 | NT | | 569,050 | 613,066 |
| | | | 696,373 | | | | 590,737 | |
| | | | 262,854 | | | | 679,410 | |
| | 13 | 20 min. | 1,009,588 | 1,194,601 | NT | | 852,141 | 1,037,128 |
| | | | 1,472,753 | | | | 1,041,371 | |
| | | | 1,101,463 | | | | 1,217,872 | |
| | 7 | 11 min. | | | 731,593 | 664,309 | | NT |
| | | | | | 543,160 | | | |
| | | | | | 718,173 | | | |
| 0.35 g | 7 | 11 min. | 1,772,021 | 1,822,683 | NT | | 1,342,768 | 1,491,564 |
| | | | 1,817,222 | | | | 1,740,035 | |
| | | | 1,878,805 | | | | 1,391,889 | |
| | 1 | 11 min. | NT | | 896,736 | 1,066,980 | | NT |
| | | | | | 1,329,122 | | | |
| | | | | | 975,083 | | | |

TABLE 6-continued

Comparison between the reference method and methods which could meet the criteria for this invention for the lysis of yeast cells

| Mass of lysing beads | Number of glass beads | Lysis time | Percentage of 100 μm beads | | | | | |
|---|---|---|---|---|---|---|---|---|
| | | | 20% | | 50% | | 80% | |
| | | | Readings | Mean | Readings | Mean | Readings | Mean |
| | 13 | 11 min. | | NT | 1,429,173<br>1,439,611<br>1,588,337 | 1,485,707 | | NT |
| | 7 | 2 min. | | NT | 323,207<br>271,399<br>388,199 | 327,602 | | NT |
| | 7 | 20 min. | | NT | 2,655,347<br>2,620,069<br>2,321,318 | 2,532,245 | | NT |
| | 7 | 11 min. | | NT | 1,519,280<br>1,503,048<br>1,375,956 | 1,466,095 | | NT |
| 0.6 g | 1 | 2 min. | 509,952<br>278,641<br>349,239 | 379,277 | | NT | 60,273<br>105,730<br>76,940 | 80,981 |
| | 13 | 2 min. | 1,070,276<br>794,021<br>725,931 | 863,409 | | NT | 234,974<br>467,140<br>260,342 | 320,819 |
| | 1 | 20 min. | 2,856,141<br>3,176,777<br>2,825,049 | 2,952,656 | | NT | 1,767,239<br>1,412,744<br>1,682,354 | 1,620,779 |
| | 13 | 20 min. | 1,826,409<br>2,156,630<br>2,017,243 | 2,000,094 | | NT | 1,500,483<br>816,002<br>372,770 | 896,418 |
| | 7 | 11 min. | | NT | 2,257,042<br>1,868,266<br>2,104,986 | 2,076,765 | | NT |

Figure 4:
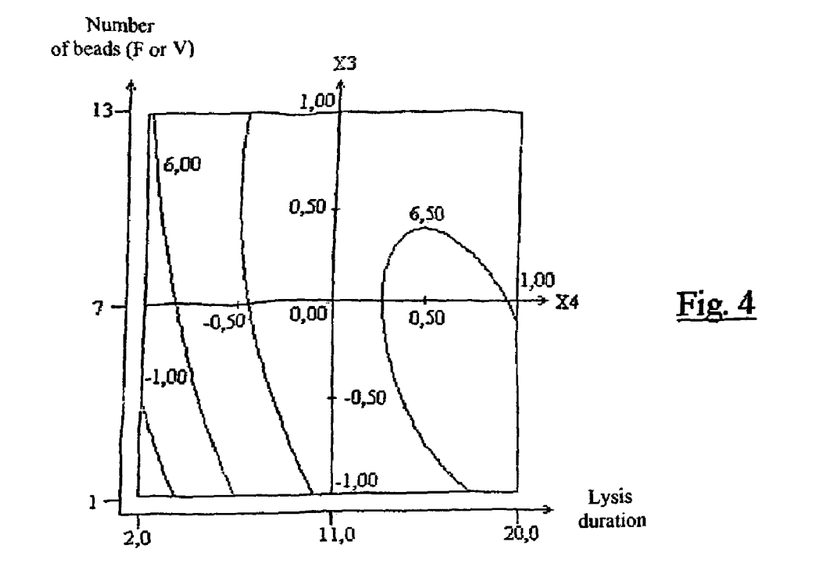
FIG. 4 shows isoresponse curves for the lysis of yeast cells by mechanical vortex centrifugation.

FIG. 4 shows the resultant isoresponse curves. Analysis of the curves shows that the most influential factor is lysis time. For maximum efficacy, a lysis time of 20 minutes is required with less than 50% beads with a diameter of 100 μm, a total mass of lysing beads of greater than 0.35 g, and fewer than seven (7) glass beads.

An example of isoresponse curves is given for a total mass of 0.5 g and a percentage of 100 μm beads of 20%.

It is shown that, in order to enhance the response, a lysis time of over 11 minutes is required with less than 50% beads with a diameter of 100 μm, a total mass of lysing beads of greater than 0.35 g, and fewer than seven (7) glass beads.

A) Mechanical Vortex Centrifugation and Bacteria

The reference protocol is based on a total mass of lysing beads of 0.6 g, a percentage of 100 μm beads of 100%, 6 glass beads, 10 iron beads, and a lysis time of 2 minutes. The corresponding HPA readings are 107 406, 124 609 and 138 405, i.e. a mean of 123 473.

The results are shown in Table 7.

TABLE 7

Comparison between the reference method and methods which could meet the criteria for this invention for the lysis of bacteria by mechanical vortex centrifugation

| Mass of lysing beads | Number of glass beads | Lysis time | Percentage of 100 μm beads | | | | | |
|---|---|---|---|---|---|---|---|---|
| | | | 20% | | 50% | | 80% | |
| | | | Readings | Mean | Readings | Mean | Readings | Mean |
| 0.1 g | 1 | 2 min. | 52,553<br>74,120<br>70,675 | 65,783 | | NT | 63,184<br>58,656<br>58,185 | 60,008 |
| | 13 | 2 min. | 14,521<br>119,746<br>39,993 | 58,087 | | NT | 41,586<br>54,066<br>40,387 | 45,346 |
| | 1 | 20 min. | 342,532<br>192,353<br>422,974 | 319,286 | | NT | 143,231<br>141,178<br>141,240 | 141,883 |
| | 13 | 20 min. | 180,946<br>152,548 | 166,747 | | NT | 62,916<br>33,591<br>89,886 | 62,131 |

TABLE 7-continued

Comparison between the reference method and methods which could meet the criteria for this invention for the lysis of bacteria by mechanical vortex centrifugation

| Mass of lysing beads | Number of glass beads | Lysis time | Percentage of 100 μm beads | | | | | |
|---|---|---|---|---|---|---|---|---|
| | | | 20% | | 50% | | 80% | |
| | | | Readings | Mean | Readings | Mean | Readings | Mean |
| | 7 | 11 min. | NT | NT | 95,433<br>89,768<br>81,290 | 88,830 | | NT |
| 0.35 g | 7 | 11 min. | 96,363<br>82,168<br>138,530 | 105,687 | | NT | 164,967<br>133,405<br>146,659 | 148,344 |
| | 1 | 11 min. | | NT | 182,124<br>134,177<br>97,015 | 137,772 | | NT |
| | 13 | 11 min. | | NT | 79,136<br>58,570<br>71,041 | 69,582 | | NT |
| | 7 | 2 min. | | NT | 68,180<br>55,805<br>42,366 | 55,450 | | NT |
| | 7 | 20 min. | | NT | 326,925<br>229,725<br>142,933 | 233,194 | | NT |
| | 7 | 11 min. | | NT | 103,348<br>90,163<br>96,770 | 96,760 | | NT |
| 0.6 g | 1 | 2 min. | 54,446<br>49,842 | 52,154 | | NT | 108,236<br>82,578<br>130,014 | 106,943 |
| | 13 | 2 min. | 80,796<br>63,431 | 72,113 | | NT | 102,979<br>162,136<br>104,830 | 123,315 |
| | 1 | 20 min. | 275,653<br>153,372<br>249,164 | 226,063 | | NT | 255,286<br>265,434<br>223,440 | 248,053 |
| | 13 | 20 min. | 189,947<br>107,754<br>112,081 | 136,594 | | NT | 176,619<br>183,820<br>185,692 | 182,044 |
| | 7 | 11 min. | | NT | 131,318<br>121,488<br>153,508 | 135,438 | | NT |

Figure 5:
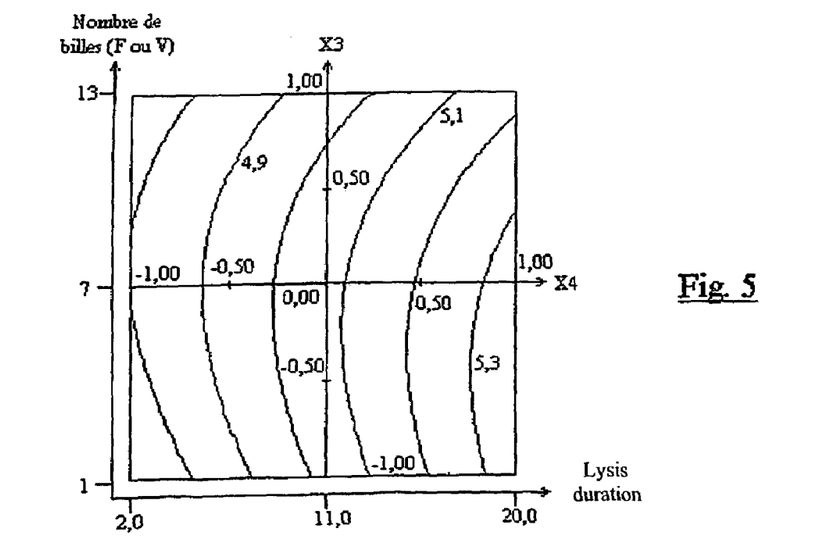
FIG. 5 shows isoresponse curves for the lysis of bacterial cells by mechanical vortex centrifugation.

FIG. 5 shows the resultant isoresponse curves. Analysis of the curves shows that the most influential factor is lysis time. To enhance the response, a maximum lysis time of 20 minutes is necessary, and the number of glass beads must be low. Moreover, the response is slightly better with a percentage of 100 μm beads of 20%, and a total mass of lysing beads close to 0.6 g although these two factors have less of an effect.

Example curves are given for a fixed, total mass of lysing beads of 0.6 g, and a fixed percentage of 100 μm beads of 20%. This is the case for FIG. 5.

The curves show that lysis time has a major effect on the response, the maximum response being obtained with a lysis time of 20 minutes. The number of glass beads has less of an effect on lytic efficiency with one single bead sufficing.

C) Selecting a Universal Protocol for Lysis by Mechanical Vortex Centrifugation

The universal protocol is therefore defined by the following parameters:
 a lysis time of 20 minutes,
 percentage of beads with a diameter of 100% m=20%,
 total mass of lysing beads=0.5 g, and
 one (1) glass bead with a diameter of substantially 3 mm.

In these conditions, the following surprising results are obtained:

the mean obtained for bacteria is 226 063 whereas the reference protocol based on only 100 μm beads gave a response of only 123 473,
the mean obtained for yeast cells is 2 952 656 whereas the reference protocol based on only 500 μm beads gave a response of only 2 105 519,
The method associated with this universal lysis protocol consists therefore in performing mechanical vortex centrifugation with the following parameters:
a lysis time of between 11 and 20 minutes, preferably between 15 and 20 minutes, and more preferably still of 20 minutes,
a percentage of beads with a diameter of 100 μm of under 30%, preferably under 30%, and more preferably still of 20%, and
a total mass of lysing beads of over 60%, preferably over 80%, and more preferably still of 100% of the total mass of the processed biological sample, and
less than seven (7) glass beads, preferably just one (1).

V: RESULTS FOR LYSIS BY MAGNETIC VORTEX CENTRIFUGATION ACCORDING TO THE INVENTION

An ERM study is not necessary in this case because of the parameters studied and their more restricted effect.

Similar experiments to those described above carried out for magnetic vortex centrifugation show that the 100 μm beads are more effective than 500 μm beads for lysing both bacteria and yeast cells.

The aim is to define, using beads with a diameter of 100 μm, optimum conditions for universal lysis based on magnetic vortex centrifugation.

The conditions investigated are:
the total amount of 100 μm beads,
the number of iron beads, and
lysis time.

A) Magnetic Vortex Centrifugation and Yeast Cells

The reference protocol is based on a total mass of lysing beads of 0.5 g, a percentage of 100 μm beads of 0% (i.e. exclusively beads with a diameter of 500 μm), 10 iron beads, and a lysis time of 12 minutes. The mean reading is 852 648.

The results obtained are presented in Table 8 below.

TABLE 8

Comparison between the reference method and methods which could meet the criteria for this invention for the lysis of bacteria by magnetic vortex centrifugation

| Total mass of lysing beads | 0.5 g | | | | 0.6 g | | | |
|---|---|---|---|---|---|---|---|---|
| Number of iron beads | 5 | | 10 | | 5 | | 10 | |
| Lysis time | 12 min. | 20 min. | 12 min. | 20 min. | 12 min. | 20 min. | 12 min. | 20 min. |
| Mean | 905,871 | 994,733 | 1,321,176 | 1,511,558 | 799,621 | 926,658 | 1,326,085 | 1,541,946 |

These results confirm that the 100 μm beads are more effective than 500 μm beads. The third condition gives a higher reading (1 321 176) than the reference condition Nevertheless, there is no substantial difference between 0.5 and 0.6 g.

Both the number of iron beads and lysis time have an effect; the best results are obtained with 10 iron beads and a 20-minute lysis time.

B) Magnetic Vortex Centrifugation and Bacteria:

The reference protocol is based on a total mass of lysing beads of 0.6 g, a percentage of 100 μm beads of 100%, 10 iron beads, and a lysis time of 10 minutes. The mean reading is 72 942.

The results obtained are presented in Table 9 below.

TABLE 9

Comparison between the reference method and methods which could meet the criteria for this invention for the lysis of bacteria by magnetic vortex centrifugation

| Total mass of lysing beads | 0.5 g | | | | 0.6 g | | | |
|---|---|---|---|---|---|---|---|---|
| Number of iron beads | 5 | | 10 | | 5 | | 10 | |
| Lysis time | 12 min. | 20 min. | 12 min. | 20 min. | 12 min. | 20 min. | 12 min. | 20 min. |
| Mean | 50,613 | 69,614 | 70,589 | 84,779 | 58,461 | 71,676 | 79,985 | 103,190 |

The total mass of lysing beads has little effect, but HPA readings are slightly higher with 0.6 g of 100 μm beads than with 0.5 g. Both the number of iron beads and lysis time have an effect; the best results are obtained with 10 iron beads and a 20-minute lysis time.

C) Selecting a Universal Protocol

The optimum conditions for both bacteria and yeast cells are the following:

0.6 g of beads with a diameter of 100 μm,
10 iron beads, and
a lysis time of 20 minutes.

These conditions referred to as universal are, remarkably, more effective than the conditions referred to as reference conditions, as is shown in Table 10 below.

TABLE 10

Comparison between the reference methods and methods which could meet the criteria for this invention for the lysis of bacteria and yeast cells by magnetic vortex centrifugation

| | Yeast cells | Bacteria |
|---|---|---|
| Reference protocol | 852,648 | 72,942 |
| Universal protocol | 1,541,946 | 103,190 |

The method associated with this universal lysis protocol consists therefore in performing magnetic vortex centrifugation with the following parameters:

a lysis time of between 12 and 20 minutes, preferably between 15 and 20 minutes, and more preferably still of 20 minutes, a total mass of lysing beads corresponding to over 80% and preferably 100% of the total mass of the processed biological sample, and between five (5) and fifteen (15) iron beads, preferably ten (10) iron beads.

VI. CONCLUSION

It is demonstrated that for all three techniques—sonication, mechanical vortex centrifugation and magnetic vortex centrifugation—universal protocols can be defined, i.e. protocols which can be used to lyse prokaryotic and/or eukaryotic cells with identical efficacy and, in many cases, superior efficacy to that of the protocols referred to as reference protocols.

The invention claimed is:

1. A method for lysing cells, comprising providing a sample containing prokaryotic cells, eukaryotic cells or a mixture of both prokaryotic cells and eukaryotic cells;
adding a plurality of lysing beads to said sample;
lysing said cells using one method selected from the group consisting of sonication and mechanical vortex centrifugation for up to 20 minutes, thereby producing a processed biological sample; wherein at least three of the following parameters (a) through (d) are satisfied:
(a) the lysing beads comprise small-diameter beads and large diameter beads, with an amount of said small-diameter beads corresponding to 50% or less than an amount of said large-diameter beads;
(b) a mass of the lysing beads is from 50 to 100% of a mass of the processed biological sample;
(c) the lysing step is performed for a time of from 10 to 20 minutes;
(d) 7 or less non-lysing glass beads are added to said sample prior to lysing to drive the movement of the lysing beads;
wherein a diameter of the smaller lysing beads is between 90 and 150 μm, and wherein a diameter of the larger lysing beads is between 400 and 600 μm.

2. The method of claim 1, wherein the lysing beads are made of glass.

3. The method of claim 1, wherein the sonication is performed under the following parameters:
a lysis time of between 9 and 20 minutes,
a percentage of beads with a diameter of 100 μm of between 10 and 50%, and
a total mass of lysing beads corresponding to between 50 and 100% of the total mass of the processed biological sample.

4. The method of claim 1, wherein the mechanical vortex centrifugation is performed under the following parameters:
a lysis time of between 11 and 20 minutes,
a percentage of beads with a diameter of 100 μm of under 50%,
a total mass of lysing beads of over 60%, of the total mass of the processed biological sample, and
less than seven glass beads.

5. The method of claim 1, wherein the diameter of the smaller lysing beads is about 100 μm, and the diameter of the larger lysing beads is about 500 μm.

6. The method of claim 3, wherein said lysis time is between 12 and 18 minutes, said percentage of beads with a diameter of 100 μm is between 20 and 30%, and said total mass of lysing beads corresponds to 75 to 90% of the processed biological sample.

7. The method of claim 6, wherein said lysing time is 15 minutes, said percentage of beads with a diameter of 100 μm is 20% and said total mass of lysing beads is between 80 and 85% of said processed biological sample.

8. The method of claim 4, wherein said lysis time is between 15 and 20 minutes, said percentage of beads with a diameter of 100 μm is under 30%, said total mass of lysing beads is over 80% and wherein there is a single glass bead employed.

9. The method of claim 8, wherein said lysis time is 20 minutes, said percentage of beads with a diameter of 100 μm is 20%, and said total mass of lysing beads is 100% of said processed biological sample.

* * * * *

UNITED STATES PATENT AND TRADEMARK OFFICE
CERTIFICATE OF CORRECTION

PATENT NO. : 7,723,095 B2
APPLICATION NO. : 10/343109
DATED : May 25, 2010
INVENTOR(S) : Philippe Cleuziat, Sandra Incardona and Corinne Jay It is certified that error appears in the above-identified patent and that said Letters Patent is hereby corrected as shown below:

Title Page item (75) of the bibliographic data, "Lyons (FR)" should read -- Lyon (FR) -- at both occurrences.

Title Page item (73) of the bibliographic data, "Mary l'Etoile (FR)" should read -- Marcy l'Etoile (FR) --

The following entry should be added to the bibliographic data:

Title Page item -- (30) Foreign Application Priority Data

Jul. 27, 2000    (FR) ............................ 00 09820 --

Signed and Sealed this
Seventeenth Day of May, 2011

David J. Kappos
*Director of the United States Patent and Trademark Office*